US008268332B2

(12) United States Patent
Manstein

(10) Patent No.: US 8,268,332 B2
(45) Date of Patent: Sep. 18, 2012

(54) METHOD FOR DERMATOLOGICAL TREATMENT USING CHROMOPHORES

(75) Inventor: Dieter Manstein, Boston, MA (US)

(73) Assignee: The General Hospital Corporation, Boston, MA (US)

(*) Notice: Subject to any disclaimer, the term of this patent is extended or adjusted under 35 U.S.C. 154(b) by 1372 days.

(21) Appl. No.: 10/599,519

(22) PCT Filed: Apr. 1, 2005

(86) PCT No.: PCT/US2005/011338
§ 371 (c)(1),
(2), (4) Date: Jun. 22, 2007

(87) PCT Pub. No.: WO2005/107848
PCT Pub. Date: Nov. 17, 2005

(65) Prior Publication Data
US 2007/0264288 A1 Nov. 15, 2007

Related U.S. Application Data

(60) Provisional application No. 60/558,476, filed on Apr. 1, 2004.

(51) Int. Cl.
*A61K 9/00* (2006.01)
(52) U.S. Cl. .................................................... 424/400
(58) Field of Classification Search .................. 424/400
See application file for complete search history.

(56) References Cited

U.S. PATENT DOCUMENTS

| | | | |
|---|---|---|---|
| 1,706,161 A | 3/1929 | Hollnagel |
| 2,472,385 A | 6/1949 | Rollman |
| 3,327,712 A | 6/1967 | Kaufman et al. |
| 3,486,070 A | 12/1969 | Engel |
| 3,527,932 A | 9/1970 | Thomas |
| 3,538,919 A | 11/1970 | Meyer |
| 3,597,652 A | 8/1971 | Gates, Jr. |
| 3,622,743 A | 11/1971 | Muncheryan |
| 3,653,778 A | 4/1972 | Freiling |
| 3,693,623 A | 9/1972 | Harte et al. |
| 3,818,914 A | 6/1974 | Bender |
| 3,834,391 A | 9/1974 | Block |
| 3,846,811 A | 11/1974 | Nakamura et al. |
| 3,857,015 A | 12/1974 | Clark et al. |
| 3,900,034 A | 8/1975 | Katz |
| 4,233,493 A | 11/1980 | Nath |
| 4,273,109 A | 6/1981 | Enderby |
| 4,275,335 A | 6/1981 | Ishida |
| 4,298,005 A | 11/1981 | Mutzhas |
| 4,316,467 A | 2/1982 | Muckerheide |
| 4,388,924 A | 6/1983 | Weissman et al. |
| 4,456,872 A | 6/1984 | Froeschle |
| 4,461,294 A | 7/1984 | Baron |
| 4,524,289 A | 6/1985 | Hammond et al. |
| 4,539,987 A | 9/1985 | Nath et al. |
| 4,561,440 A | 12/1985 | Kubo et al. |
| 4,591,762 A | 5/1986 | Nakamura |
| 4,608,978 A | 9/1986 | Rohr |
| 4,617,926 A | 10/1986 | Sutton |
| 4,686,986 A | 8/1987 | Fenyo et al. |
| 4,695,697 A | 9/1987 | Kosa |
| 4,718,416 A | 1/1988 | Nanaumi |
| 4,733,660 A | 3/1988 | Itzkan |
| 4,745,909 A | 5/1988 | Pelton et al. |
| 4,747,660 A | 5/1988 | Nishioka et al. |
| 4,749,913 A | 6/1988 | Stuermer et al. |
| 4,819,669 A | 4/1989 | Politzer |
| 4,832,024 A | 5/1989 | Boussignac et al. |
| 4,860,172 A | 8/1989 | Schlager et al. |
| 4,860,744 A | 8/1989 | Johnson et al. |
| 4,884,560 A | 12/1989 | Kuracina |
| 4,905,690 A | 3/1990 | Ohshiro et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos et al. |
| 4,945,239 A | 7/1990 | Wist et al. |
| 4,973,848 A | 11/1990 | Kolobanov et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |

(Continued)

FOREIGN PATENT DOCUMENTS

WO     WO 91/02562     3/1991

OTHER PUBLICATIONS

Tachihara et al. "Percutaneous Drug Delivery Using Er:Yag Laser". Lasers in Surgery and Medicine: The Offficial Journal of the American Society for Laser Medicine and Surgery, Inc. American Society for Laser Medicine and Surgery Twenty-Second Annual Meeting. Atlanta, Georgia. Apr. 10-14, 2002 Abstracts. p. 29, Item 129.

(Continued)

*Primary Examiner* — Fereydoun G Sajjadi
*Assistant Examiner* — Audrea Buckley
(74) *Attorney, Agent, or Firm* — Dorsey & Whitney LLP

(57) ABSTRACT

The present invention encompasses methods that use heat and/or electromagnetic radiation for dermatological treatment and more particularly to a method that uses heat and/or electromagnetic radiation in combination with chromophores for fractional wounding and, in particular, discontinuous fractional damage of skin tissue.

24 Claims, No Drawings

U.S. PATENT DOCUMENTS

| | | | |
|---|---|---|---|
| 5,066,293 A | 11/1991 | Furumoto |
| 5,071,417 A | 12/1991 | Sinofsky |
| 5,108,388 A | 4/1992 | Trokel |
| 5,127,395 A | 7/1992 | Bontemps |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,267,399 A | 12/1993 | Johnston |
| 5,282,797 A | 2/1994 | Chess |
| 5,287,380 A | 2/1994 | Hsia |
| 5,300,097 A | 4/1994 | Lerner et al. |
| 5,304,170 A | 4/1994 | Green |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,342,358 A | 8/1994 | Daikuzono |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,358,503 A | 10/1994 | Bertwell et al. |
| 5,380,317 A | 1/1995 | Everett et al. |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,454,807 A | 10/1995 | Lennox et al. |
| 5,458,140 A | 10/1995 | Eppstein et al. |
| 5,474,549 A | 12/1995 | Ortiz et al. |
| 5,486,172 A | 1/1996 | Chess |
| 5,505,726 A | 4/1996 | Meserol |
| 5,505,727 A | 4/1996 | Keller |
| 5,519,534 A | 5/1996 | Smith |
| 5,522,813 A | 6/1996 | Trelles |
| 5,531,739 A | 7/1996 | Trelles |
| 5,531,740 A | 7/1996 | Black |
| 5,549,660 A | 8/1996 | Mendes et al. |
| 5,558,667 A | 9/1996 | Yarborough et al. |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,653,706 A | 8/1997 | Zavislan et al. |
| 5,655,547 A | 8/1997 | Karni |
| 5,658,148 A | 8/1997 | Neuberger et al. |
| 5,658,323 A | 8/1997 | Miller |
| 5,660,836 A | 8/1997 | Knowlton |
| 5,662,643 A | 9/1997 | Kung et al. |
| 5,662,644 A | 9/1997 | Swor |
| 5,669,916 A | 9/1997 | Anderson |
| 5,683,380 A | 11/1997 | Eckhouse et al. |
| 5,698,866 A | 12/1997 | Doiron et al. |
| 5,707,401 A | 1/1998 | Talmore |
| 5,707,403 A | 1/1998 | Grove et al. |
| 5,720,772 A | 2/1998 | Eckhouse |
| 5,722,397 A | 3/1998 | Eppstein |
| 5,728,090 A | 3/1998 | Martin et al. |
| 5,735,844 A | 4/1998 | Anderson et al. |
| 5,735,884 A | 4/1998 | Thompson et al. |
| 5,742,392 A | 4/1998 | Anderson et al. |
| 5,743,901 A | 4/1998 | Grove et al. |
| 5,746,735 A | 5/1998 | Furumoto et al. |
| 5,755,751 A | 5/1998 | Eckhouse |
| 5,759,200 A | 6/1998 | Azar |
| 5,769,076 A | 6/1998 | Maekawa et al. |
| 5,782,249 A | 7/1998 | Weber et al. |
| 5,810,801 A | 9/1998 | Anderson et al. |
| 5,814,008 A | 9/1998 | Chen et al. |
| 5,814,040 A | 9/1998 | Nelson et al. |
| 5,814,041 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,827,264 A | 10/1998 | Hohla |
| 5,828,803 A | 10/1998 | Eckhouse |
| 5,830,208 A | 11/1998 | Muller |
| 5,836,877 A | 11/1998 | Zavislan |
| 5,836,998 A * | 11/1998 | Mueller et al. ............... 607/95 |
| 5,836,999 A | 11/1998 | Eckhouse et al. |
| 5,840,048 A | 11/1998 | Cheng |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,871,480 A | 2/1999 | Tankovich |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,893,828 A | 4/1999 | Uram |
| 5,908,418 A | 6/1999 | Dority et al. |
| 5,913,883 A | 6/1999 | Alexander et al. |
| 5,916,211 A | 6/1999 | Quon et al. |
| 5,920,374 A | 7/1999 | Vaphiades et al. |
| 5,944,748 A | 8/1999 | Mager et al. |
| 5,948,011 A | 9/1999 | Knowlton |
| 5,949,222 A | 9/1999 | Buono |
| 5,954,710 A | 9/1999 | Paolini et al. |
| 5,955,490 A | 9/1999 | Kennedy et al. |
| 5,964,749 A | 10/1999 | Eckhouse et al. |
| 5,968,033 A | 10/1999 | Fuller |
| 5,968,034 A | 10/1999 | Fullmer et al. |
| 5,977,723 A | 11/1999 | Yoon |
| 5,984,915 A | 11/1999 | Loeb et al. |
| 6,015,404 A | 1/2000 | Altshuler et al. |
| 6,022,316 A | 2/2000 | Eppstein et al. |
| 6,026,828 A | 2/2000 | Altshuler |
| 6,027,495 A | 2/2000 | Miller |
| 6,030,399 A | 2/2000 | Ignotz et al. |
| 6,032,071 A | 2/2000 | Binder |
| RE36,634 E | 3/2000 | Ghaffari |
| 6,036,684 A | 3/2000 | Tankovich et al. |
| 6,050,990 A | 4/2000 | Tankovich et al. |
| D424,197 S | 5/2000 | Sydlowski et al. |
| 6,056,738 A | 5/2000 | Marchitto et al. |
| 6,059,820 A | 5/2000 | Baronov |
| 6,074,382 A | 6/2000 | Asah et al. |
| 6,080,146 A | 6/2000 | Altshuler et al. |
| 6,080,147 A | 6/2000 | Tobinick |
| 6,086,580 A | 7/2000 | Mordon et al. |
| 6,094,767 A | 8/2000 | Iimura |
| 6,096,029 A | 8/2000 | O'Donnell, Jr. |
| 6,096,209 A | 8/2000 | O'Brien et al. |
| 6,099,521 A | 8/2000 | Shadduck |
| 6,104,959 A | 8/2000 | Spertell |
| 6,117,129 A | 9/2000 | Mukai |
| 6,120,497 A | 9/2000 | Anderson |
| 6,142,650 A | 11/2000 | Brown et al. |
| 6,142,939 A | 11/2000 | Eppstein et al. |
| 6,149,644 A | 11/2000 | Xie |
| 6,162,055 A | 12/2000 | Montgomery et al. |
| 6,162,211 A | 12/2000 | Tankovich et al. |
| 6,162,212 A | 12/2000 | Kreindel et al. |
| 6,171,301 B1 | 1/2001 | Nelson |
| 6,173,202 B1 | 1/2001 | Eppstein et al. |
| 6,174,325 B1 | 1/2001 | Eckhouse |
| 6,176,854 B1 | 1/2001 | Cone |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,197,020 B1 | 3/2001 | O'Donnell |
| 6,200,134 B1 | 3/2001 | Kovac et al. |
| 6,200,309 B1 | 3/2001 | Rice et al. |

| | | | | | |
|---|---|---|---|---|---|
| 6,210,425 B1 | 4/2001 | Chen | 6,723,090 B2 | 4/2004 | Altshuler et al. |
| 6,214,034 B1 | 4/2001 | Azar | 6,743,222 B2 | 6/2004 | Durkin et al. |
| 6,228,075 B1 | 5/2001 | Furumoto | 6,770,069 B1 | 8/2004 | Hobart et al. |
| 6,229,831 B1 | 5/2001 | Nightingale et al. | 6,790,205 B1 | 9/2004 | Yamazaki et al. |
| 6,235,016 B1 | 5/2001 | Stewart | 6,801,595 B2 | 10/2004 | Grodzins et al. |
| 6,236,891 B1 | 5/2001 | Ingle et al. | 6,808,532 B2 | 10/2004 | Andersen et al. |
| 6,245,093 B1 | 6/2001 | Li et al. | RE38,670 E | 12/2004 | Asah et al. |
| 6,263,233 B1 | 7/2001 | Zavislan et al. | 6,862,771 B1 | 3/2005 | Muller |
| 6,264,649 B1 | 7/2001 | Whitcroft et al. | 6,878,144 B2 | 4/2005 | Altshuler et al. |
| 6,267,779 B1 | 7/2001 | Gerdes | 6,881,212 B1 | 4/2005 | Clement et al. |
| 6,267,780 B1 | 7/2001 | Streeter | 6,887,260 B1 | 5/2005 | McDaniel |
| 6,273,884 B1 | 8/2001 | Altshuler et al. | 6,888,319 B2 | 5/2005 | Inochkin et al. |
| 6,273,885 B1 | 8/2001 | Koop et al. | 6,974,451 B2 | 12/2005 | Altshuler et al. |
| 6,280,438 B1 | 8/2001 | Eckhouse et al. | 6,976,985 B2 | 12/2005 | Altshuler et al. |
| 6,283,956 B1 | 9/2001 | McDaniel | 6,997,923 B2 | 2/2006 | Anderson et al. |
| 6,290,713 B1 | 9/2001 | Russell | 7,001,413 B2 | 2/2006 | Butler |
| 6,306,130 B1 | 10/2001 | Anderson et al. | 7,006,223 B2 | 2/2006 | Mullani |
| 6,306,160 B1 | 10/2001 | Nidetzky | 7,029,469 B2 | 4/2006 | Vasily |
| 6,319,274 B1 | 11/2001 | Shadduck | 7,044,959 B2 | 5/2006 | Anderson et al. |
| 6,331,111 B1 | 12/2001 | Cao | 7,060,061 B2 | 6/2006 | Altshuler et al. |
| 6,340,495 B1 | 1/2002 | Sumian et al. | 7,077,840 B2 | 7/2006 | Altshuler et al. |
| 6,343,933 B1 | 2/2002 | Montgomery et al. | 7,097,656 B1 | 8/2006 | Akopov et al. |
| 6,350,276 B1 | 2/2002 | Knowlton | 2001/0023363 A1 | 9/2001 | Harth et al. |
| 6,354,370 B1 | 3/2002 | Miller et al. | 2001/0024777 A1 | 9/2001 | Azar et al. |
| 6,358,272 B1 | 3/2002 | Wilden | 2001/0041886 A1 | 11/2001 | Durkin et al. |
| 6,383,176 B1 | 5/2002 | Connors et al. | 2002/0005475 A1 | 1/2002 | Zenzie |
| 6,383,177 B1 | 5/2002 | Balle-Petersen et al. | 2002/0019624 A1 | 2/2002 | Clement |
| 6,387,089 B1 | 5/2002 | Kreindel et al. | 2002/0026225 A1 | 2/2002 | Segal |
| 6,402,739 B1 | 6/2002 | Neev | 2002/0091311 A1* | 7/2002 | Eppstein et al. ............... 600/309 |
| 6,406,474 B1 | 6/2002 | Neuberger et al. | 2002/0091377 A1 | 7/2002 | Anderson |
| 6,413,267 B1 | 7/2002 | Dumoulin-White et al. | 2002/0111610 A1 | 8/2002 | Nordquist |
| 6,424,852 B1 | 7/2002 | Zavislan | 2002/0123745 A1 | 9/2002 | Svaasand et al. |
| 6,425,912 B1 | 7/2002 | Knowlton | 2002/0128635 A1 | 9/2002 | Altshuler et al. |
| 6,436,094 B1 | 8/2002 | Reuter | 2002/0161357 A1 | 10/2002 | Anderson et al. |
| 6,440,155 B1 | 8/2002 | Matsumae et al. | 2002/0161418 A1 | 10/2002 | Wilkens et al. |
| 6,451,007 B1 | 9/2002 | Koop et al. | 2002/0173780 A1 | 11/2002 | Altshuler et al. |
| 6,461,296 B1 | 10/2002 | Desai | 2003/0004499 A1 | 1/2003 | McDaniel |
| 6,471,712 B2 | 10/2002 | Burres | 2003/0018373 A1 | 1/2003 | Eckhardt et al. |
| 6,471,716 B1 | 10/2002 | Pecukonis | 2003/0023235 A1 | 1/2003 | Cense et al. |
| 6,475,211 B2 | 11/2002 | Chess et al. | 2003/0023283 A1 | 1/2003 | McDaniel |
| 6,494,900 B1 | 12/2002 | Salansky et al. | 2003/0023284 A1 | 1/2003 | Gartstein et al. |
| 6,508,785 B1 | 1/2003 | Eppstein | 2003/0032900 A1 | 2/2003 | Ella |
| 6,508,813 B1 | 1/2003 | Altshuler | 2003/0032950 A1 | 2/2003 | Altshuler et al. |
| 6,511,475 B1 | 1/2003 | Altshuler et al. | 2003/0036680 A1 | 2/2003 | Black |
| 6,514,243 B1 | 2/2003 | Eckhouse et al. | 2003/0055414 A1 | 3/2003 | Altshuler et al. |
| 6,517,532 B1 | 2/2003 | Altshuler et al. | 2003/0057875 A1 | 3/2003 | Inochkin et al. |
| 6,527,764 B1 | 3/2003 | Neuberger et al. | 2003/0065314 A1 | 4/2003 | Altshuler et al. |
| 6,530,915 B1 | 3/2003 | Eppstein et al. | 2003/0083649 A1 | 5/2003 | Margaron et al. |
| 6,537,270 B1 | 3/2003 | Elbrecht et al. | 2003/0100936 A1 | 5/2003 | Altshuler et al. |
| 6,547,780 B1 | 4/2003 | Sinofsky | 2003/0109787 A1 | 6/2003 | Black |
| 6,554,439 B1 | 4/2003 | Teicher et al. | 2003/0109860 A1 | 6/2003 | Black |
| 6,558,372 B1 | 5/2003 | Altshuler | 2003/0129154 A1 | 7/2003 | McDaniel |
| 6,565,532 B1* | 5/2003 | Yuzhakov et al. ............ 604/142 | 2003/0159615 A1* | 8/2003 | Anderson et al. .......... 106/31.03 |
| 6,569,155 B1 | 5/2003 | Connors et al. | 2003/0169433 A1 | 9/2003 | Koele et al. |
| 6,572,637 B1 | 6/2003 | Yamazaki et al. | 2003/0187486 A1 | 10/2003 | Savage et al. |
| 6,600,951 B1 | 7/2003 | Anderson | 2003/0195494 A1 | 10/2003 | Altshuler et al. |
| 6,602,245 B1 | 8/2003 | Thiberg | 2003/0199859 A1 | 10/2003 | Altshuler et al. |
| 6,605,080 B1 | 8/2003 | Altshuler et al. | 2003/0216795 A1 | 11/2003 | Harth et al. |
| 6,605,083 B2 | 8/2003 | Clement et al. | 2003/0232303 A1 | 12/2003 | Black |
| 6,629,971 B2 | 10/2003 | McDaniel | 2004/0006332 A1 | 1/2004 | Black |
| 6,629,989 B2 | 10/2003 | Akita | 2004/0010298 A1 | 1/2004 | Altshuler et al. |
| 6,632,219 B1 | 10/2003 | Baranov et al. | 2004/0015156 A1 | 1/2004 | Vasily |
| 6,635,075 B2 | 10/2003 | Li et al. | 2004/0015158 A1 | 1/2004 | Chen et al. |
| 6,641,578 B2 | 11/2003 | Mukai | 2004/0024388 A1 | 2/2004 | Altshuler |
| 6,641,600 B1 | 11/2003 | Kohler | 2004/0030326 A1 | 2/2004 | Altshuler et al. |
| 6,648,904 B2 | 11/2003 | Altshuler et al. | 2004/0034319 A1 | 2/2004 | Anderson et al. |
| 6,653,618 B2 | 11/2003 | Zenzie | 2004/0034341 A1 | 2/2004 | Altshuler et al. |
| 6,659,999 B1 | 12/2003 | Anderson et al. | 2004/0073079 A1 | 4/2004 | Altshuler et al. |
| 6,660,000 B2 | 12/2003 | Neuberger et al. | 2004/0082940 A1 | 4/2004 | Black et al. |
| 6,663,620 B1 | 12/2003 | Altshuler et al. | 2004/0085026 A1 | 5/2004 | Inochkin et al. |
| 6,663,658 B1 | 12/2003 | Kollias et al. | 2004/0093042 A1 | 5/2004 | Altshuler et al. |
| 6,663,659 B2 | 12/2003 | McDaniel | 2004/0111132 A1 | 6/2004 | Shenderova et al. |
| 6,676,654 B1 | 1/2004 | Balle-Petersen et al. | 2004/0133251 A1 | 7/2004 | Altshuler et al. |
| 6,679,837 B2 | 1/2004 | Daikuzono | 2004/0143920 A1 | 7/2004 | Nanda |
| 6,685,699 B1 | 2/2004 | Eppstein et al. | 2004/0147984 A1 | 7/2004 | Altshuler et al. |
| 6,689,124 B1 | 2/2004 | Thiberg | 2004/0162549 A1 | 8/2004 | Altshuler et al. |
| 6,706,035 B2 | 3/2004 | Cense et al. | 2004/0162596 A1 | 8/2004 | Altshuler et al. |
| 6,709,269 B1 | 3/2004 | Altshuler | 2004/0176754 A1 | 9/2004 | Island et al. |
| 6,709,446 B2 | 3/2004 | Lundahl et al. | 2004/0191729 A1 | 9/2004 | Altshuler et al. |

| | | |
|---|---|---|
| 2004/0193235 A1 | 9/2004 | Altshuler et al. |
| 2004/0193236 A1 | 9/2004 | Altshuler et al. |
| 2004/1019323 | 9/2004 | Butler |
| 2004/0199227 A1 | 10/2004 | Altshuler et al. |
| 2004/0204745 A1 | 10/2004 | Altshuler et al. |
| 2004/0210276 A1 | 10/2004 | Altshuler et al. |
| 2004/0214132 A1 | 10/2004 | Altshuler |
| 2004/0225339 A1 | 11/2004 | Yaroslavsky et al. |
| 2004/0230258 A1 | 11/2004 | Altshuler et al. |
| 2005/0038418 A1 | 2/2005 | Altshuler et al. |
| 2005/0049582 A1 | 3/2005 | DeBenedictis et al. |
| 2005/0049658 A1 | 3/2005 | Connors et al. |
| 2005/0107849 A1 | 5/2005 | Altshuler et al. |
| 2005/0168158 A1 | 8/2005 | Inochkin et al. |
| 2005/0171517 A1 | 8/2005 | Altshuler et al. |
| 2005/0197681 A1 | 9/2005 | Barolet et al. |
| 2005/0215988 A1 | 9/2005 | Altshuler et al. |
| 2006/0004306 A1 | 1/2006 | Altshuler et al. |
| 2006/0004347 A1 | 1/2006 | Altshuler et al. |
| 2006/0009750 A1 | 1/2006 | Altshuler et al. |
| 2006/0020309 A1 | 1/2006 | Altshuler et al. |
| 2006/0058712 A1 | 3/2006 | Altshuler et al. |
| 2006/0122668 A1 | 6/2006 | Anderson et al. |
| 2006/0149343 A1 | 7/2006 | Altshuler et al. |
| 2006/0161143 A1 | 7/2006 | Altshuler et al. |
| 2006/0194164 A1 | 8/2006 | Altshuler et al. |
| 2006/0206103 A1 | 9/2006 | Altshuler et al. |
| 2006/0253176 A1 | 11/2006 | Caruso et al. |
| 2006/0271028 A1 | 11/2006 | Altshuler et al. |
| 2006/0287646 A1 | 12/2006 | Altshuler et al. |
| 2007/0027440 A1 | 2/2007 | Altshuler et al. |
| 2007/0038206 A1 | 2/2007 | Altshuler et al. |
| 2007/0049910 A1 | 3/2007 | Altshuler et al. |
| 2007/0060819 A1 | 3/2007 | Altshuler et al. |
| 2007/0067006 A1 | 3/2007 | Altshuler et al. |
| 2007/0073308 A1 | 3/2007 | Anderson et al. |
| 2007/0078501 A1 | 4/2007 | Altshuler et al. |
| 2007/0194717 A1 | 8/2007 | Belikov et al. |
| 2007/0198004 A1 | 8/2007 | Altshuler et al. |
| 2007/0213696 A1 | 9/2007 | Altshuler et al. |
| 2007/0213698 A1 | 9/2007 | Altshuler et al. |
| 2007/0213792 A1 | 9/2007 | Yaroslavsky et al. |
| 2007/0219604 A1 | 9/2007 | Yaroslavsky et al. |
| 2007/0219605 A1 | 9/2007 | Yaroslavsky et al. |
| 2007/0239142 A1 | 10/2007 | Altshuler et al. |
| 2007/0239143 A1 | 10/2007 | Altshuler et al. |
| 2007/0255355 A1 | 11/2007 | Altshuler et al. |

OTHER PUBLICATIONS

International Search Report and Written Opinion of the International Searching Authority of PCT/US05/011083 dated Nov. 26, 2007.

* cited by examiner

METHOD FOR DERMATOLOGICAL TREATMENT USING CHROMOPHORES

INCORPORATION BY REFERENCE

This application claims priority to U.S. provisional patent application No. 60/558,476, filed Apr. 1, 2004.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to methods that use heat and/or electromagnetic radiation for dermatological treatment and, more particularly to a method that uses heat and/or electromagnetic radiation and chromophores to ablate or damage selected portions of a target area for dermatological treatment.

BACKGROUND OF THE INVENTION

There is an increasing demand for repair of or improvement to skin defects, which can be induced by aging, sun exposure, dermatological diseases, traumatic effects, and the like. Many treatments which use electromagnetic radiation have been used to improve skin defects by inducing a thermal injury to the skin, which results in a complex wound healing response of the skin. This leads to a biological repair of the injured skin.

Various techniques providing this objective have been introduced in recent years. The different techniques can be generally categorized in two groups of treatment modalities: ablative laser skin resurfacing ("LSR") and non-ablative collagen remodeling ("NCR"). The first group of treatment modalities, i.e., LSR, includes causing thermal damage to the epidermis and/or dermis, while the second group, i.e., NCR, is designed to spare thermal damage of the epidermis.

LSR with pulsed $CO_2$ or Er:YAG lasers, which may be referred to in the art as laser resurfacing or ablative resurfacing, is considered to be an effective treatment option for signs of photo aged skin, chronically aged skin, scars, superficial pigmented lesions, stretch marks, and superficial skin lesions. However, patients may experience major drawbacks after each LSR treatment, including edema, oozing, and burning discomfort during first fourteen (14) days after treatment. These major drawbacks can be unacceptable for many patients. A further problem with LSR procedures is that the procedures are relatively painful and therefore generally require an application of a significant amount of analgesia. While LSR of relatively small areas can be performed under local anesthesia provided by injection of an anestheticum, LSR of relatively large areas is frequently performed under general anesthesia or after nerve blockade by multiple injections of anesthetic.

Any LSR treatment results in thermal skin damage to the treatment area of the skin surface, including the epidermis and/or the dermis. LSR treatment with pulsed $CO_2$ lasers is particularly aggressive, causing thermal skin damage to the epidermis and at least to the superficial dermis. Following LSR treatment using $CO_2$ lasers, a high incidence of complications can occur, including persistent erythema, hyperpigmentation, hypopigmentation, scarring, and infection (e.g., infection with Herpes simplex virus). LSR treatment with the Er:YAG laser has been introduced as a more gentle alternative to the $CO_2$ laser, due to the lesser penetration depth of the Er:YAG pulsed laser. Using the Er:YAG laser results in a thinner zone of thermal injury within the residual tissue of the target area of the skin. However, LSR that uses the Er:YAG laser produces side effects similar to those made by LSR that uses the $CO_2$ laser within the first days after treatment.

A limitation of LSR using $CO_2$ or Er:YAG lasers is that ablative laser resurfacing generally can not be performed on the patients with dark complexions. The removal of pigmented epidermis tissue can cause severe cosmetic disfigurement to patients with a dark complexion, which may last from several weeks up to years, which is considered by most patients and physicians to be unacceptable. Another limitation of LSR is that ablative resurfacing in areas other than the face generally have a greater risk of scarring. LSR procedures in areas other than the face result in an increased incidence of an unacceptable scar formation because the recovery from skin injury within these areas is not very effective.

In an attempt to overcome the problems associated with LSR procedures, a group of NCR techniques has emerged. These techniques are variously referred to in the art as non-ablative resurfacing, non-ablative subsurfacing, or non-ablative skin remodeling. NCR techniques generally utilize non-ablative lasers, flashlamps, or radio frequency current to damage dermal tissue while sparing damage to the epidermal tissue. The concept behind NCR techniques is that the thermal damage of only the dermal tissues is thought to induce wound healing which results in a biological repair and a formation of new dermal collagen. This type of wound healing can result in a decrease of photoaging related structural damage. Avoiding epidermal damage in NCR techniques decreases the severity and duration of treatment related side effects. In particular, post procedural oozing, crusting, pigmentary changes and incidence of infections due to prolonged loss of the epidermal barrier function can usually be avoided by using the NCR techniques.

Various strategies are presently applied using nonablative lasers to achieve damage to the dermis while sparing the epidermis. Nonablative lasers used in NCR procedures have a deeper dermal penetration depth as compared to ablative lasers used in LSR procedures. Wavelengths in the near infrared spectrum can be used. These wavelengths cause the non-ablative laser to have a deeper penetration depth than the very superficially-absorbed ablative Er:YAG and $CO_2$ lasers. The dermal damage is achieved by a combination of proper wavelength and superficial skin cooling, or by focusing a laser into the dermis with a high numerical aperture optic in combination with superficial skin cooling. While it has been demonstrated that these techniques can assist in avoiding epidermal damage, one of the major drawbacks of these techniques is their limited efficacies. The improvement of photoaged skin or scars after the treatment with NCR techniques is significantly smaller than the improvements found when LSR ablative techniques are utilized. Even after multiple treatments, the clinical improvement is often far below the patient's expectations. In addition, clinical improvement is usually several months delayed after a series of treatment procedures.

Another limitation of NCR procedures relates to the breadth of acceptable treatment parameters for safe and effective treatment of dermatological disorders. The NCR procedures generally rely on an optimum coordination of laser energy and cooling parameters, which can result in an unwanted temperature profile within the skin leading to either no therapeutic effect or scar formation due to the overheating of a relatively large volume of the tissue.

Yet another problem of non-ablative procedures relates to the sparing of the epidermis. While sparing the epidermis is advantageous in order to decrease the side effects related to complete removal of the epidermis, several applications of NCR procedures may benefit from at least partial removal of epidermal structures. For example, photoinduced skin aging manifests not only by the dermal alterations, but also by epidermal alterations.

A further problem of both ablative and nonablative resurfacing is that the role of keratinocytes in the wound healing response is not capitalized upon. Keratinocyte plays an active role in the wound healing response by releasing cytokines when the keratinocyte is damaged. During traditional ablative resurfacing procedures, the keratinocytes are removed from the skin along with the epidermis, thereby removing them from the healing process altogether. On the other hand, in traditional non-ablative procedures, the keratinocytes, which are located in the epidermis, are not damaged, therefore they do not release cytokines to aid in the healing process.

Another major problem with all LSR and NCR techniques now used is the appearance of visible spots and/or edges after treatment due to inflammation, pigmentation, or texture changes, corresponding to the sites of treatment. Devices for LSR and NCR produce macroscopic (easily seen) exposure areas. For example, laser exposure spot diameters typically vary from about 1 to 10 mm, and NCR exposure spot diameters from about 3 to 50 mm. Some devices, such as intense pulsed light devices, leave "boxes" of skin response due to rectangular output patterns on the skin. Patients do not like such spot or box patterns, easily seen as red, brown or white areas ranging from on the order of millimeters to centimeters in size, which remain for days or even years after treatment.

Therefore, there is a need to provide a procedure that combine safe and effective treatment for improvement of dermatological disorders while reducing or eliminating undesirable side effects such as intra-procedural discomfort, post-procedural discomfort, lengthy healing time, and post-procedural infection.

Citation or identification of any document in this application is not an admission that such document is available as prior art to the present invention.

SUMMARY OF THE INVENTION

It is an object of the present invention to provide a method that combines safe and effective treatment for an improvement of dermatological disorders with minimal undesirable side effects. Another object of the present invention is to provide a method that simultaneously causes a pattern of individual microscopic wounds to a portion of a target area while sparing portions of the skin adjacent to the wounds from damage. Still another object of the present invention is to provide a method that successively causes multiple microscopic wounds to a region of skin being treated.

These and other objects can be achieved with an exemplary embodiment of the method according to the present invention, in which at least portions of a target area are subjected electromagnetic radiation, e.g., heat, light, radio frequency pulses, etc. In accordance with the methods of the present invention electromagnetic radiation may be applied invasively or non-invasively to portions of a target area, causing fractional wounding within this region of skin.

In an advantageous embodiment of the present invention, portions of the skin tissue are indirectly heated using one or more chromophores that preferentially absorb electromagnetic radiation. In one advantageous embodiment, one or more chromophores are placed in registration with selected portions of the skin surface within the target area in a pattern corresponding to the desired fractional wounding. Electromagnetic radiation may be applied according to the methods of the present invention whereby the chromophores preferentially absorb the electromagnetic radiation and transfer heat to adjacent portions of the skin, thus creating a fractional wounding pattern in the region of skin being treated.

In yet still another embodiment of the present invention, pigment particles, e.g., chromophores, may be distributed within the skin and may preferentially absorb electromagnetic radiation that is applied to the region of skin being treated, causing fractional wounding within the target area. Advantageously, a mask with a pattern corresponding to the desired fractional wounding can also be applied, such that fractional wounding occurs where the mask is in contact with skin, i.e., a "positive mask." Alternatively, a mask can be configured to protect the skin from fractional wounding, e.g., fractional wounding occurs on the unprotected portion of the skin, which constitutes a "negative mask."

It is noted that in this disclosure and particularly in the claims and/or paragraphs, terms such as "comprises," "comprised," "comprising" and the like can have the meaning attributed to it in U.S. Patent law; e.g., they can mean "includes," "included," "including," and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

The exemplary methods in accordance with the present invention deliver energy in the form of heat and/or electromagnetic radiation to a target area of skin on a patient, wherein such energy is selectively absorbed in various patterns so as to induce thermal injury corresponding to the patterns. In the present disclosure, 'skin' refers to both the dermis and the epidermis, separately or collectively. The term 'dermal tissue' is also used interchangeably with the term 'skin' herein. The resulting regions of thermal injury involve only a fraction of the target area of skin. The delivery of the heat and/or electromagnetic radiation to the target area in a predetermined pattern is achieved using either invasive or noninvasive delivery apparatus and methods to generate a specific pattern for affecting superficial and/or sub-dermal thermal skin injury. "Thermal injury" encompasses cell death in one or more regions of the dermal tissue of interest ("lethal damage"), or stimulation of the release of cytokines, heat shock proteins, and other wound healing factors without stimulating necrotic cell death ("sublethal damage"). "Damage" is used interchangeably with "thermal injury" herein. The term "target area" refers to any region of skin being treated in accordance with the present invention. The term "fractional wounding" refers to any method or process that results in regions of damaged skin that are small in at least one dimension (where "small" is approximately 1 mm. or less), and where such damaged regions have at least one adjacent region of undamaged skin tissue that may be large.

Fractional wounding encompasses the controlled ablation, removal, destruction, damage or stimulation of multiple regions of epidermal skin tissue, generally having at least one dimension smaller than about 1 mm, while sparing intervening areas of skin tissue from damage. The damage may optionally extend into the dermal tissue below the epidermis. Fractional wounding also encompasses creation of damaged regions of tissue within the dermis. It is performed to achieve beneficial cosmetic and medical results by mechanisms such as tissue reshaping and stimulation of wound healing responses. The spatial scale of fractional wounding is chosen to allow for rapid wound healing and to avoid the appearance of spots or scars on a macroscopic scale, while still providing effective treatment by exposing multiple small areas to greater than a minimal damaging stimulus. For example, damaging individual exposure areas approximately 0.1 mm diameter and spaced about 0.2 mm apart, extending into the skin up to a depth of about 0.5 mm, is well tolerated. This type of damage pattern produces effective improvement of photoaging of skin and rapid healing of the affected area, while avoiding the formation of apparent spots. Spared skin between the individual damaged areas assists in promoting a rapid wound healing response.

During the exemplary fractional wounding procedure of the present invention, certain portions of the target area remain undamaged, thereby preserving keratinocytes and melanocytes, which serve as a source of undamaged cells to promote reepithelialization. This procedure differs from traditional resurfacing procedures, wherein the entirety of the target area is damaged, thus inhibiting the ability of the damaged areas to heal.

The fractional wounding patterns employed in accordance with the present invention may be oval, circular, arced, linear, irregular and/or the like, or any combination thereof, in shape. In a preferred embodiment, the specific pattern may comprise one or more lines, wherein such lines may be straight or curved and may have a constant or varying width. Patterns may also be formed by straight or curved lines, intersecting lines, discontinuous lines, or various combinations thereof. In other embodiments, wavy patterns may be used. A wavy pattern includes, but is not limited to, one or more circular, arced and otherwise irregular non-linear lines. A wavy pattern may result in a feathered edge, which avoids a sharp macroscopically visible demarcation between treated and untreated areas.

Alternatively, patterns employed in accordance with the present invention may comprise a dispersion of dots or other discontinuous domains. The dots may be round, oval, ovoid, or the like. Patterns may also comprise any combination of dots and lines. Line patterns may also be advantageous for achieving directional shrinkage or other anisotropic effects. For example, a line pattern may be generated parallel to skin wrinkles for directed shrinkage of the wrinkles.

After the dermatological treatment disclosed herein is completed, portions of the target area of the skin are damaged in a specific pattern. The smallest dimension of any damaged region of skin tissue is preferably in the range of about 1 μm to about 1000 μm, or about 100 μm to about 800 μm, or about 300 μm to about 500 μm.

The fill factor for a fractional wounding procedure represents the relative amounts of damaged and undamaged tissue after treatment is performed. This factor is important because it denotes the amount of undamaged tissue that is available to initiate and promote the wound healing process in the damaged areas. If tissue damage is induced primarily at or near the surface of the skin (e.g., within the epidermis), a fill factor can be defined as the percentage of the surface area of the target area that is damaged tissue. If damage is induced primarily within the dermis, or extends from the surface to the skin down to a characteristic depth in the skin, the fill factor can be defined as the volumetric percentage of damaged tissue within the overall volume of treated skin. The overall volume of treated skin can be defined as the size of the target area multiplied by the distance between the uppermost and lowermost damaged regions of tissue within the target area.

The fill factor in accordance with the present invention can be about 10% to about 80%, preferably about 20% to about 70%, more preferably about 30% to about 60%, and most preferably about 40%. The preferred fill factor for a given treatment may vary with the specific condition or imperfections in the skin being treated and the wound healing response desired.

The average distance between individual regions of damaged tissue may be in the range between about 10 μm to about 2000 μm, and preferably in the range of about 100 μm to about 500 μm. The macroscopic pattern of the individual damaged areas may be a field of uniformly distributed individual damaged areas having nearly constant spacing throughout the target area, randomly distributed individual damaged areas within the target area, and/or regularly distributed individual damaged areas with uniform spacing and randomly shifted locations.

The skin treatment in accordance with the present invention can be performed in by a single treatment covering the skin surface with a specific surface damage pattern, or by multiple treatments either performed at the same visit or during different treatment visits. Individual or multiple exposures can be used to achieve the appropriate thermal damage in particular target areas. Employing regularly distributed individual damaged areas with uniform spacing and randomly shifted locations may be useful to minimize undesirable effects that may occur during multiple treatments of a given target area. Such multiple treatments may be utilized to cover the entire area as homogeneously as possible by the individual damaged areas over the course of multiple treatments, while allowing healing to occur between individual treatments. Uniformly distributed individual damaged areas with constant spacing throughout the target area may create unwanted spatial distributions similar to moiré patterns, resulting in spatial interference macroscopic patterns generated with a distance in between the areas of exposure which have a significant spatial period. To minimize the occurrence of moiré patterns, a randomized shift within the range of about 10% to about 50% of the average distance between individual damaged areas during a single treatment may be utilized.

In an embodiment in accordance with the present invention, a chromophore may be placed on portions of the surface of the epidermal tissue of the target area or deposited within the epidermal tissue or dermal tissue in a pattern or distribution. The target area is then heated or exposed to an electromagnetic radiation source. The chromophore may absorb the electromagnetic radiation and transfer a portion of this absorbed energy in the form of heat to adjacent portions of the target area in sufficient amounts to cause local thermal damage. In an advantageous embodiment, the chromophore is distributed on or in the epidermal or dermal tissue in a pattern corresponding to the desired pattern of fractional wounding, e.g., over a tattooed portion of the skin, or in linear patterns parallel or perpendicular to a set of wrinkles.

The present invention encompasses the application of a specific pattern of chromophores to a target area of skin, followed by exposure of the target area to heat or electromagnetic energy, to induce the formation of fractional wounding.

The pattern may be directly applied to the skin using chromophores in a suitable form, such as those suspended in an ink or a gel. In an alternate embodiment, the chromophores are first applied uniformly over the target area, and the fractional wounding pattern is determined by a mask. The mask employed in accordance with this embodiment of the present invention is preferably a reflective shield (a "negative" mask). The chromophore will preferential absorb incident energy directed toward the target area to promote wounding in the underlying skin, whereas the reflective mask will protect the portions of the target area beneath it from wounding. The reflective negative mask determines the pattern of undamaged skin that remains after the target area is exposed to heat or energy. The portions of the target area not covered by this mask correspond to the resultant fractional wounding patterns.

In another embodiment, the fractional wounding pattern is achieved by initially applying the one or more chromophores as a layer, optionally in the form of a powder or suspended in a liquid or other solvent. Next, a portion of the one or more chromophores is selectively removing from the surface of the skin. The residual chromophores that remain on or in the skin are preferentially located on or within particular features of the skin to be treated, such as pores or wrinkles. In this way, the subsequent fractional wounding pattern will preferentially damage the targeted features that the residual chromophores are associated with.

In other advantageous embodiments, chromophore particles are selectively distributed on or in the epidermal or dermal tissue of the patient. In one exemplary embodiment, large chromophore particles may be matched to the anatomical structure of the skin profile, e.g., the chromophore may be distributed over epidermal tissue that contains dilated pores by brushing a light-absorbing powder over the skin surface. The chromophore powder may then cover the epidermal tissue with a heterogeneous thickness, with a greater concentration of chromophore within the pores. Subsequent exposure of the target area to heat or electromagnetic radiation may then lead to preferential absorption of heat sufficient to cause greater thermal damage the unwanted dilated pore than to the surrounding areas.

In an exemplary embodiment according to the present invention, pigment particles, e.g., a chromophore, ink, dye and the like, may be distributed within the selected portions of the target area of the epidermis or dermis prior to application of electromagnetic radiation to thereby cause fractional wounding of the selected portions of the target area. The pigment particles preferentially absorb the electromagnetic radiation, causing an increase in the temperature of the pigment particles that damages the selected portions of the target area in local contact with the pigment particles. In some embodiments, the pigment particles may be randomly distributed within the skin to cause fractional wounding of a large portion of a target area. In other embodiments, the pigment particles may be controllably distributed by using a preferred particle concentration and diameter.

In other embodiments, a delivery apparatus may be used to place chromophores in a portion of the target area. Any device that results in application of a discontinuous pattern of chromophores on or within the skin may be utilized in the methods of the invention. A desired pattern of chromophores may be applied by a grid, a mesh, a roller, a stamp or a stencil. Advantageously, the pattern is applied with a grid or a mesh, preferably a metal grid or mesh. In another example, a needle stamp, comprising a chromophore at the tips of the needles, may be used to deliver the chromophore to the surface of the skin or within the epidermis or within the dermis at a preferred depth. In an exemplary embodiment, the chromophore particles may be removable after treatment of the target area, e.g., with a second application of electromagnetic radiation of a different wavelength.

In another embodiment, the specific pattern of the one or more chromophores is applied to the skin using an attachment medium. The attachment medium may be an adhesive, a solvent, or a light-activated material. Advantageously, the attachment medium is an acrylide, a derma-bond or a glue. In a preferred embodiment, the attachment medium is applied to a grid, a mesh, a roller, a stamp, or a stencil prior to application of the one or more chromophores to the grid, mesh, roller, stamp or stencil to facilitate the delivery of the one or more chromophores to the skin. Alternatively, the attachment medium may be deposited onto the skin in the desired pattern, and a uniform coating of the desired chromophore is then deposited over the entire target area in a continuous or near-continuous layer. The applied chromophore that does not overlie the attachment medium is then removed by mechanical or other means, such as brushing or blowing off with compressed air, leaving a pattern of chromophore that adheres to the underlying patterned attachment medium.

In another advantageous embodiment, a stencil is used to form the patterns for chromophore deposition and subsequent wounding. A stencil containing cutout patterns of the desired wounded regions is placed over the target area. A chromophore suspended in a solvent or in any other form that will adhere to exposed skin is then applied uniformly over the stencil. The stencil is then removed, leaving a pattern of chromophores on the target area that is subsequently exposed to heat or radiation to induce fractional wounding.

The present invention also encompasses a method for fractional wounding of skin, comprising applying one or more chromophores to a target area, followed by application of a mask with a specific pattern over the target area, wherein the specific pattern corresponds to a desired pattern of fractional wounding. The target area is then exposed to heat and/or electromagnetic radiation. In one embodiment, the mask preferentially absorbs energy and the chromophore is reflective, such that the fractional wounding occurs where the mask is in contact with the skin. In another embodiment, the mask is reflective and protects portions of the skin from fractional wounding, and the fractional wounding occurs where the skin is not in contact with the mask, aided by the presence of chromophores that preferentially absorb energy. The mask can be a grid, a mesh, a roller, a stamp or a stencil. Advantageously, the mask is a mesh. Preferably, the mesh comprises one or more metals. The fractional wounding methods employing masks in accordance with the present invention are distinguished from those of International Publication No. WO 2004/086947 in that the present invention utilizes chromophores to enhance and better control the fractional damage.

The surface of the mask should preferably have a minimal absorption at the wavelength generated by the electromagnetic radiation source for the particular dermatological process. Such absorption can decrease the undesirable heating of the mask. The mask may be coated by one or more chromophore reflectors, e.g., a metal material, for affectuating a minimal absorption of the electromagnetic radiation. Additionally, the microstructure of the mask can have a periodicity preferably in the range of the wavelength of the electromagnetic radiation emitted by the delivery optics. This configuration can diffuse the collimated electromagnetic radiation emitted by the delivery optics into a highly scattered beam so as to decrease the risk of electromagnetic radiation-related accidents. In another exemplary embodiment, the microstructure of the surface of the mask may have a periodicity in the range of the wavelength of the electromagnetic radiation emitted by the delivery optics.

The mask may also have a configuration so as to provide effective skin cooling during the exposure thereof with the radiation. Skin cooling provides significant anesthetic effects, and has other advantages related to the pattern induced by the electromagnetic radiation. The mask can be cooled prior to the beginning of the dermatological procedure, during the procedure by spraying an evaporative agent or a precooled liquid onto the mask between the successive electromagnetic radiation pulses, or during the procedure by introducing a cool or cold liquid into microchannels running through the mask. The cooling of the mask has a secondary advantage in that such cooling of the mask decreases the rate of the electromagnetic radiation absorption by the mask, as the rate of the electromagnetic radiation absorption by the metals increases with the increasing temperature.

To provide skin cooling as described above, the temperature of the mask should be in the range of about 37 C to about −20 C, and preferably about 10 C to about −4 C. The mask can both protect and cool the portions of the skin surface that are not exposed to electromagnetic radiation emitted by the electromagnetic radiation source. In addition to cooling and shielding portions of the skin surface, the mask allows the debris ejected during ablative procedures to escape, and thereby not interfere with the beam delivery for successive pulses. For example, the areas that are not exposed to the laser are being cooled by the mask, i.e., the areas that are provided between the affected areas.

In another exemplary embodiment, all areas (i.e., both the affected and nonaffected areas) are cooled to provide anesthesia, and to reduce over-damaging the superficial levels of the damaged areas. A cooling agent, e.g., either a liquid or gas, may circulate through microchannels during a dermatological procedure, thereby removing heat from the protected skin and the mask itself.

In another embodiment, a masking function is achieved by depositing a pattern of reflective chromophores that protect the skin beneath the pattern from damage. The damage is induced in the exposed skin not covered by reflective chromophores upon exposure of the target area to heat or electromagnetic radiation. The mask of this embodiment differs from the mask of PCT publication WO 2004/086947 in that the mask of the present invention is an applied layer that may comprise one or more chromophore reflectors to shield the skin from heat and/or electromagnetic radiation, and is not a separable apparatus.

In an advantageous embodiment, the one or more chromophore reflectors include, but are not limited to, a glass bead, a gold flake, a metal particle (e.g., gold, silver, or copper), a mirrored glass bead, a salt crystal, a silica, or any combination thereof.

Any chromophore that is non-toxic that preferably causes minimal irritation to skin may be contemplated in the methods of the present invention (see, e.g., U.S. Patent Application Publication Nos. 2001/0013349, 2003/0159615 and 2003/0050678). A preferred chromophore in the methods of the present invention is a very strong absorbing chromophore that will make a fine pattern on the skin. In an advantageous embodiment, the chromophore comprises carbon. In this embodiment, a wavelength in the range of about 400 nm to about 1200 nm is applied.

In another advantageous embodiment, the chromophore can be a phase transition chromophore. Preferably, the phase transition chromophore may comprise paraffin. The paraffin melting during application of heat and/or electromagnetic energy can protect portions of the skin, generally by absorbing some of the incident energy to accomplish the phase transition. The phase transition chromophore may also protect underlying thermal damage if the chromophore is in a matrix, such as but not limited to paraffin or polymers that melt after laser heating but do not cause skin damage upon melting. In one embodiment of the present invention, phase transition chromophores may be employed to form a positive mask. A pattern of the phase transition chromophore is deposited onto the target area such that it covers the portions of the skin that are not to undergo thermal damage. The target area is then exposed to heat or other electromagnetic energy. The portions of the target area not covered by the phase transition chromophore will be damaged, whereas the portions of the target area protected by this chromophore will be spared from damage because the phase transition chromophore will absorb some or all of the incident heat or energy. The result of this process is a pattern of fractional damage over the target area that spares those portions of the skin initially covered by the phase change chromophore. It is routine experimentation of one of skill in the art to adjust the intensity and/or exposure time of the energy or heat source to achieve desired results for a particular application.

As used herein, a chromophore includes compounds having chromophoric groups such as nitro groups, azo, alkylene units, esters, carbonyl groups, aldehydes, alkynes, aromatic rings, heterocyclics, carboxylic acids and the like. The chromophore acts to selectively absorb the chosen wavelength of laser light thereby enhancing the effectiveness of the irradiation. Other chromophores or photoactive or photoabsorbable compounds can be used which themselves act as therapeutic or cytotoxic agents upon irradiation. A chromophore also may be a substance (solid, liquid, or gas) that has color or imparts a color to the intact microparticles (including when the substance itself lacks color, for example, a clear gas, but scatters electromagnetic waves, for example, light, and thus may appear colored, for example, white, blue, green, or yellow, depending on its scattering properties) under some conditions, for example, all of the time or after exposure to a certain wavelength (such as in a fluorescent substance). For example, a chromophore can be a fluorescent, phosphorescent, wavelength up-converting, or other substance that may normally be substantially invisible, but that emits ultraviolet, visible, or infrared wavelengths during and/or after exposure to wavelengths from a particular region of the electromagnetic spectrum. A chromophore can also be a substance that reversibly or irreversibly changes color spontaneously or in response to any stimulus. The chromophore can be or include rifampin, β-carotene, tetracycline, indocyanine green, Evan's blue, methylene blue, FD&C Blue No. 1 (Brilliant Blue FCF), FD&C Green No. 3 (Fast Green FCF), FD&C Red No. 3 (Erythrosine), FD&C Red No. 40, FD&C Yellow No. 5 (Tartrazine), or FD&C Yellow No. 6 (Sunset Yellow FCF). The chromophore can be any colored substance approved by the United States Food and Drug Administration for use in humans. In certain embodiments, the chromophore can be detected by the naked eye under normal lighting conditions or when exposed to UV, near-UV, IR, or near-IR radiation.

As used herein, a microparticle may be a particle of a relatively small size, not necessarily in the micron size range; the term is used in reference to particles of sizes that can be implanted to form tissue markings and thus can be less than 50 nm to 100 microns or greater. In contrast, a nanoparticle may be a particle in the nanometer ($10^{-9}$) size range, for example, 15 nm or 500 nm. A micro- or nanoparticle may be of composite construction and is not necessarily a pure substance; it may be spherical or any other shape. Microparticles include (i) an indispersible, biologically inert coating, (ii) a core enveloped within the coating, wherein the core includes the chromophore which is detectable through the coating and is dispersible in the tissue upon release from the microparticle, and, optionally, (iii) an absorption component that absorbs the specific energy and that is located in the coating or the core, or both; and the specific property is the absorption of the specific energy to rupture the microparticle, releasing the chromophore which disperses in the tissue, thereby changing or removing, or both, the detectable marking, wherein the coating, the core, or the optional absorption component, or any combination thereof, provides the specific property.

Chromophores can be made from any appropriate solid, liquid, or gaseous material that has chromophoric properties. In general, useful chromophores include stains, dyes, colored drugs and proteins, and other materials. Preferably, chromophores are biologically inert and/or non-toxic (ideally they are non-carcinogenic, non-allergenic, and non-immunogenic) such as those approved by the FDA for use within the body.

Chromophores may be mixed in combinations before or after optional encapsulation, so that it may only be necessary to select a small number of different chromophores to obtain a broad range of colors for various tissue marking purposes. For example, the pure chromophores can be encapsulated separately and afterwards different colors may be mixed to form intermediate colors and shades (yellow microparticles may be mixed with blue microparticles to form a green mixture). Combinations of two or more unreactive chromophores can be mixed to form desired colors and shades, and then encapsulated to form microparticles. Optionally, pure chromophores may be separately encapsulated to form sub-microparticles, and then different colored sub-microparticles can be mixed together (or with unencapsulated chromophores) to form desired colors and shades. The mixture can then be encapsulated in coating to form a microparticle having a perceived color resulting from the blend of the differently colored chromophores.

Useful dispersible chromophores include, but are not limited to: drugs and dyes such as rifampin (red), β-carotene (orange), tetracycline (yellow), indocyanine green (such as Cardio-Green™), Evan's blue, methylene blue; soluble inorganic salts such as copper sulfate (green or blue), $Cu(NH_3)^{2+}$ (dark blue), $MnO_4$ (purple), $NiCl_2$ (green), $CrO_4$ (yellow), $Cr_2O_7^{2-}$ (orange); proteins such as rhodopsin (purple and yellow forms) and green fluorescent protein (fluoresces green under blue light); and any of the Food and Drug Administration (FDA) approved dyes used commonly in foods, pharmaceutical preparations, medical devices, or cosmetics, such as the well-characterized non-toxic sodium salts FD&C Blue No. 1 (Brilliant Blue FCF), FD&C Green No. 3 (Fast Green FCF), FD&C Red No. 3 (Erythrosine), FD&C Red No. 40 (ALLURA™ Red AC), FD&C Yellow No. 5 (Tartrazine), and FD&C Yellow No. 6 (Sunset Yellow FCF). Of these FD&C dyes, Yellow No. 5 is known to produce occasional allergic reactions. Additional FDA approved dyes and colored drugs are described in the Code of Federal Regulations (CFR) for Food and Drugs (see Title 21 of CFR chapter 1, parts 1-99).

Dispersible chromophore nanoparticles can be made from certain inert, normally indispersible colored substances which have been reduced to nanoparticles about 50 nm and smaller. Although diffuse nanoparticles might have different optical properties from the macroscopic material, when concentrated within the confined space of a microparticle core (that is, nanoparticles are closer together than the wavelength of visible light, about 500 nm), they act as a single light scatterer and/or absorber, and thus have the appearance of the original indispersible material from which they are derived. Useful dispersible chromophore nanoparticles may be made from graphite, iron oxides, and other materials with small particle size, for example, less than 50 nm and preferably less than 5 nm.

Like the coating material, chromophores can be a material, or can include specific absorption components, which strongly absorbs radiation of specific wavelength(s), particularly in the near-infrared spectral region from about 800 to 1800 nm. Absorption properties of the chromophore or specific absorption component allow the microparticle core to be selectively heated by pulses of near-infrared radiation, thus rupturing the microparticle and releasing the previously encapsulated chromophores.

Visibly colored near-infrared absorbing materials can be used as the chromophore(s) (to provide the desired detectable color) or as specific absorption component(s) in conjunction with another chromophore (to contribute to the detectable color, if desired). The infrared-absorbing visible chromophore should be rendered invisible upon exposure of the microparticles to the radiation, for example, through dispersal. Examples of useful colored near-infrared absorbing materials include, but are not limited to, graphite and amorphous forms of carbon (black), iron oxides (black or red), silicon (black), germanium (dark gray), cyanine dyes (including indocyanine green and other colors), phthalocyanine dyes (green-blue), and pyrylium dyes (multiple colors). See also U.S. Pat. No. 5,409,797 to Hosoi et al.

Near-infrared absorbing materials used as specific absorption component(s) can also be visibly transparent or nearly transparent at the concentrations and sizes used within the microparticles so that they do not affect the perceived color of the microparticle or of the tissue after microparticle disruption even if the material is indispersible. Useful examples include particles of filter glass (such as those manufactured by Schott, Inc.) and plastics such as polymethylmethacrylate (PMMA), as well as low concentrations of nanoparticulate graphite or other carbon. These materials can be mixed with chromophores having a desired color and then encapsulated.

Although this description has focused on near-infrared absorbing materials, materials with other properties (such as absorption of ultraviolet, visible, microwave, radio wave and other wavelengths) can also be used to construct the radiation-targeted portion of the microparticles. For example, visible materials can be incorporated into the microparticles as chromophores, or as specific absorption components within the chromophore or coating material. Then visible radiation can be applied to rupture the microparticles. Useful materials include, but are not limited to, all of the visible colored dispersible chromophores listed above and other materials rendered invisible upon exposure of the microparticles to the visible radiation, for example, Oil Nile Blue N dyes, fluorescein dyes, porphyrin dyes, and coumarin dyes.

In another embodiment, chromophores can be materials that are rendered invisible (or whose color changes) upon exposure of the microparticles to specific electromagnetic radiation without necessarily rupturing the microparticle. Bleachable chromophores (which react with a bleaching agent released by the radiation), photobleachable chromophores (altered by the radiation) or thermolabile chromophores (altered by heat produced by radiation absorption) may be used. Most of the chromophores listed above are suitable, because they can be oxidized and rendered invisible by bleaching agents, for example, peroxides, hypochlorites (such as sodium hypochlorite, or household bleach), excited oxygen species, or free radicals. For example, a microparticle can be constructed with core chromophore FD&C Red No. 40 and sub-microparticle(s) 90 containing sodium hypochlorite as the bleaching agent, which is released upon exposure of the microparticle to specific electromagnetic radiation. The chromophore FD&C Red No. 40 is rendered invisible upon exposure of the microparticle to this radiation and mixing with the bleach. Bleachable chromophores which are pH-sensitive can also be used, because they can be rendered invisible if the pH within the microparticle is changed. For example, a microparticle can be constructed with core chromophore phenolphthalein (pink to red above pH 9) in a basic alcohol solution and sub-microparticle(s) 90 containing hydrochloric acid as bleaching agent 100 which is released upon exposure of the microparticle to specific electromagnetic radiation. The chromophore phenolphthalein is rendered invisible upon exposure of the microparticle to this radiation because of reduction in pH within the microparticle.

Photobleachable chromophores that are colored until they are rendered invisible by exposure to a specific type, wavelength, and/or intensity of electromagnetic radiation include, but are not limited to, phthalocyanine (such as the zinc or chloroaluminum complexes which are green or blue); porphycenes which can be green or purple; chlorin which is a chlorophyll derivative; rhodamine dyes which can appear red, yellow, or orange and are bleached upon exposure to near-ultraviolet light; porphyrins (such as porfimer sodium, for example, PHOTOFRIN™ (Quadra Logic Technologies, Vancouver, British Columbia, Canada), a green chromophore bleached by near-ultraviolet light); Rose Bengal, bleached upon exposure to near-ultraviolet light or high intensity visible light (such as in the megawatts/cm.sup.2 range); and infrared-bleached dye-paired ion compounds, cationic dye-borate anion complexes, 3-position-substituted coumarin compounds, and bis(diiminosuccinonitrilo)-metal complexes, as described in U.S. Pat. No. 5,409,797 to Hosoi et al. Some chromophores are only photobleached upon simultaneous absorption of multiple photons, and are therefore unaffected by diffuse solar radiation.

A thermolabile chromophore may be any substance that becomes invisible upon heating through absorption of radiation by the chromophore or a component in contact with the chromophore which indirectly heats it. Thermolabile chromophoric mixtures can also be prepared by mixing a specific chromophore with a thermally initiated activator that releases free radicals upon heating. These free radicals then react chemically with the chromophore to render it invisible. The activators are used in the plastics industry for thermal curing of various plastics.

Microparticles constructed in accordance with any of the foregoing embodiments can also provide tissue markings that are normally invisible but can be detected under specific conditions or by specific devices. For example, materials that fluoresce, phosphoresce, wavelength up-convert, or otherwise emit visible light upon exposure to specific, often high-intensity wavelengths can be used in the microparticles. Substances can also be used which reversibly or irreversibly change color spontaneously or upon any of a variety of stimuli including changes in the chromophore's environment (such as temperature or pH) or upon exposure to energy (such as electromagnetic energy, for example, sunlight).

The chromophore may also be lipophilic or non-lipophilic. A lipophilic chromophore is dissolved in a pharmaceutically acceptable oil and applied directly to the area of skin one wishes to treat. A lipophilic chromophore is dissolved in oil at a final concentration from about 0.001% to about 20% (w/v), with the proportion determined empirically using an animal model (e.g., a hamster ear model or other appropriate model for human skin as known in the art).

A non-lipophilic chromophore is applied as chromophore-bearing liposomes or as a lipid, chromophore suspension. Following application of either a lipophilic chromophore in oil, chromophore-bearing liposomes or a lipid chromophore suspension, either by swabbing, for example with a cotton swab, a cotton ball or a paint brush, or by spraying or pouring the chromophore-oil mixture on the area to be treated, the mixture may be manually rubbed into the affected area to enhance the degree and/or rate of penetration of the mixture into the skin. Generally, the mixture is contacted with the skin for about 2 minutes to about 24 hours prior to irradiation. The time of contact of the mixture and the concentration of chromophore applied is determined empirically using an animal model for a given chromophore preparation. The mixture may be applied to an entire area, for example, the face, or to a smaller portion of the area (e.g., a small portion of the face or back) one ultimately wishes to treat.

The form of heat and/or energy applied to selectively induce fractional wounding of the skin in accordance with the present invention is determined, in part, by the selection of the chromophore to be used for a given treatment. The absorption properties of the chromophore determines, in part, the specific energy wavelengths to be applied. For example, if carbon is the chromophore, then a wavelength of about 400 nm to about 1200 nm is preferred. The energy source may be a laser, a flashlamp, a tungsten lamp, a diode, a diode array, and the like, or a $CO_2$ laser or a Er:YAG laser. Collimated pulsed electromagnetic irradiation may be applied which has a pulse duration in the range of about 1 µs to about 10 s, preferably in the range of about 100 µs to about 100 ms, and more preferably in the range of about 0.1 ms to about 10 ms, and fluence in the range from about 0.01 to about 100 $J/cm^2$, and preferably in the range from about 1 to about 10 $J/cm^2$. The applied electromagnetic radiation should be able to achieve at least a temperature rise within the areas of the skin that is sufficient to cause damage to the epidermis and/or the dermis. The peak temperature sufficient to cause thermal damage in the exposed tissues is time dependent and at least in the range of about 45 C to about 100 C. For exposure times in the range of about 0.1 ms to about 10 ms, the minimum temperature rise required to cause thermal damage is in the range of approximately about 60 C to about 100 C. The depth of thermal damage can be adjusted by proper choice of wavelength, fluence per pulse and number of pulses. Determination of the amount and duration of energy to be applied is routine experimentation for one of skill in the art.

In another embodiment, the applied energy may also be in part to the depth of the skin to be penetrated as described in International Publication No. WO 02/053050. The applied radiation may have an output wavelength which is at least in part a function of the at least one depth of the treatment portions. More specifically, the wavelength of the applied radiation may be selected as a function of the applied radiation as follows: depth=0.05 to 0.2 mm, wavelength=400-1880 nm & 2050-2350 nm, with 800-1850 nm & 2100-2300 nm preferred; depth=0.2 to 0.3 mm, wavelength=500-1880 nm & 2050-2350 nm, with 800-1850 nm & 2150-2300 nm preferred; depth=0.3 to 0.5 mm, wavelength=600-1380 nm & 1520-1850 nm & 2150-2260 nm, with 900-1300 nm & 1550-1820 nm & 2150-2250 nm preferred; depth=0.5 to 1.0 mm, wavelength=600-1370 nm & 1600-1820 nm, with 900-1250 nm & 1650-1750 nm preferred; depth=1.0 to 2.0 mm, wavelength=670-1350 nm & 1650-1780 nm, with 900-1230 nm preferred; depth=2.0 to 5.0 mm, wavelength=800-1300 nm, with 1050-1220 nm preferred.

Fractional wounding may cause portions of the epidermis to be thermally damaged or ablated, thereby reducing the efficacy of the barrier function of the epidermis and in particular decreasing the stratum corneum. This facilitates the delivery of drugs or specific substances to the dermis and epidermis which can either enhance the effects of the treatment, or decrease the side effects caused by partial damage of the epidermis and/or dermis. Groups of drugs and substances, which may enhance the efficacy of skin remodeling include, but are not limited to, growth factors, collagen byproducts, collagen precursors, hyaluronic acid, vitamins, antioxidants, amino acids and supplemental minerals among others. Groups of drugs and substances, which may decrease side effects, can be steroidal anti-inflammatory drugs, non-steroidal anti-inflammatory drugs, antioxidants, antibiotics, antiviral drugs, antiyeast drugs and antifungal drugs.

In an exemplary embodiment of the present invention, the vitamins that are used may be vitamin C and/or vitamin E. The supplemental minerals used are copper and zinc. The antioxidants can be vitamin C and/or vitamin E.

The fill factor of the target area may be monitored by sensing the electrical impedance of the skin from a location on the skin within the target area to a remote location on the skin outside of the target area during or after treatment. An indicator capable of staining the defects in the stratum corneum (for example, trypan glue) or transdermal water loss are effective indicators of the fill factor of the target area.

The invention is further described by the following numbered paragraphs:

1. A method for fractional wounding of skin, comprising applying
   (i) one or more chromophores in a specific pattern to a predetermined area of skin, wherein the specific pattern corresponds to a desired pattern of fractional wounding, and
   (ii) heat and/or electromagnetic radiation to the predetermined area of skin.
2. A method for fractional wounding of skin, comprising applying
   (i) one or more chromophores to a predetermined area of skin,
   (ii) a mask with a specific pattern over the predetermined area of skin, wherein the specific pattern corresponds to a desired pattern of fractional wounding, and
   (iii) heat and/or electromagnetic radiation.
3. The method of paragraph 1 or 2 wherein the method further comprises controlling an electromagnetic radiation source to generate the electromagnetic radiation.
4. The method of paragraph 3 wherein the electromagnetic radiation source comprises an ablative laser.
5. The method of paragraph 3 wherein the electromagnetic radiation source comprises one of a diode laser, a fiber laser, a solid state laser and a gas laser.
6. The method of paragraph 3 wherein the electromagnetic radiation source comprises a radio frequency generator.
7. The method of paragraph 3 wherein the electromagnetic radiation source comprises an electric power supply.
8. The method of any one of paragraphs 1 to 7 wherein the electromagnetic radiation is applied to skin through a delivery module configured to direct the electromagnetic radiation to the predetermined area of skin.
9. The method of paragraph 8 wherein the delivery module is capable of perforating the skin to a predetermined depth.
10. The method of paragraph 8 wherein the delivery module comprises a beam collimator.
11. The method of paragraph 8 wherein the delivery module comprises optical components.
12. The method of paragraph 8 wherein the delivery module comprises a light guide or fiber.
13. The method of paragraph 12, wherein the delivery module comprises a proximal portion capable of transmitting at least one light pulse and a distal portion, wherein the distal portion increases in temperature at least due to the at least one light pulse causing thermal damage to epidermal tissue and/or dermal tissue of the predetermined area within the target area of the skin.
14. The method of paragraph 12, wherein the delivery module is capable of transmitting at least one light pulse wherein the at least one light pulse directly causes damage to at least one of the epidermal tissue and/or the dermal tissue of the predetermined area within the target area of the skin.
15. The method of paragraph 8, wherein the delivery module comprises a needle.
16. The method of paragraph 15, wherein the needle is insulated.
17. The method of paragraph 15, wherein the needle is heated to cause thermal damage to epidermal tissue and/or dermal tissue of the predetermined area within the target area of the skin.
18. The method of paragraph 15, wherein the needle is capable of transmitting at least one radio frequency pulse wherein the at least one radio frequency pulse heats the needle to cause thermal damage to epidermal tissue and/or dermal tissue of the predetermined area within the target area of the skin.
19. The method of paragraph 15, wherein the needle is capable of transmitting at least one radio frequency pulse wherein the at least one radio frequency pulse directly causes damage to epidermal tissue and/or dermal tissue of the predetermined area within the target area of the skin.
20. The method of paragraph 15, wherein the needle is cooled before inserted in the epidermal tissue or dermal tissue within the target area of the skin.
21. The method of paragraph 15, wherein the needle perforates the skin to cause damage to epidermal tissue and dermal tissue of the predetermined area within the target area of the skin.
22. The method of paragraph 8, wherein the delivery module comprises particles comprising the one or more chromophores.
23. The method of paragraph 22, wherein the particles absorb electromagnetic radiation to produce heat sufficient to cause damage to epidermal tissue and/or dermal tissue of the predetermined area within the target area of the skin.
24. The method of paragraph 22, wherein the particles are placed randomly, semi-randomly or in the specific pattern on the predetermined area of skin.
25. The method of paragraph 22, wherein the particles are placed randomly, semi-randomly or in the specific pattern in at least one of the epidermal tissue and/or dermal tissue.
26. The method of paragraph 25, wherein the particles may be removed from the at least one of the epidermal tissue and/or dermal tissue.
27. The method of any one of paragraphs 8 to 26 wherein an adaptor is coupled to the delivery module providing the delivery module in communication with an electromagnetic radiation source.
28. The method of paragraph 27 wherein the adaptor is configured to mount to multiple electromagnetic radiation source.
29. The method of any one of paragraphs 1 to 28 wherein the specific pattern comprises a plurality of spatially separated individual damaged areas.

30. The method of paragraph 29, wherein dermal tissue of the skin of the plurality of spatially separated individual damaged areas is damaged down to a predetermined depth thereof.

31. The method of paragraph 29, wherein the plurality of spatially separated individual damaged areas cover at least five percent of the target area and at most sixty percent of the target area.

32. The method of paragraph 29, wherein an average distance between each of the plurality of spatially separated individual damaged areas is at least 10 μm and at most 2000 μm.

33. The method of paragraph 29, wherein each of the plurality of spatially separated individual exposure areas have a diameter of approximately 0.1 mm.

34. The method of paragraph 29, wherein each of the plurality of spatially separated individual exposure areas have a lateral diameter of a smallest dimension of at least 1 μm and at most 500 μm.

35. The method of paragraph 29, wherein a first one of the plurality of spatially separated individual exposure areas is exposed to electromagnetic radiation associated with a first set of parameters and a second one of the plurality of spatially separated individual exposure areas is exposed to electromagnetic radiation associated with a second set of parameters.

36. The method of paragraph 29, wherein at least two of the individual exposure areas are separated from one another by an unaffected area.

37. The method of paragraph 31, wherein the at least two of the individual exposure areas are separated from one another by at least approximately 125 μm.

38. The method of paragraph 31, wherein the at least two of the individual exposure areas are separated from one another by at most approximately 500 μm.

39. The method of paragraph 29, wherein one of at least one hundred of the individual exposure areas within an area of a square centimeter is separated from another one of the at least one hundred of the individual exposure areas by an unaffected area.

40. The method of paragraph 29, wherein one of at least one thousand of the individual exposure areas within an area of a square centimeter is separated from another one of the at least one thousand of the individual exposure areas by an unaffected area.

41. The method of paragraph 1 wherein the specific pattern of the one or more chromophores is applied as a layer.

42. The method of paragraph 41 wherein the layer application comprises applying the one or more chromophores to the skin and removing the one or more chromophores from the surface of the skin, wherein the one or more chromophores remain in pores of the skin.

43. The method of paragraph 42 wherein the one or more chromophores is applied to skin as a powder.

44. The method of paragraph 1 wherein the specific pattern of the one or more chromophores is applied by a grid, a mesh, a roller, a stamp or a stencil.

45. The method of any one of paragraphs 1 or 41 to 44 wherein the specific pattern of the one or more chromophores is applied to the skin with an attachment medium.

46. The method of paragraph 45 wherein the attachment medium is an adhesive.

47. The method of paragraph 45 or 46 wherein the attachment medium is light-activated.

48. The method of any one of paragraphs 45 to 47 wherein the attachment medium is an acrylide, a derma-bond or a glue.

49. The method of any one of paragraphs 45 to 48 wherein the attachment medium is applied to a grid, a mesh, a roller, a stamp or a stencil prior to application of the one or more chromophores.

50. The method of paragraph 2 wherein the fractional wounding occurs where the mask is in contact with the skin.

51. The method of paragraph 50 wherein the mask is a grid, a mesh, a roller, a stamp or a stencil.

52. The method of paragraph 51 wherein the mask is a mesh.

53. The method of paragraph 52 wherein the mesh comprises one or more metals.

54. The method of paragraph 2 wherein the mask protects the skin from fractional wounding and wherein the fractional wounding occurs where the skin is not in contact with the mask.

55. The method of paragraph 54 wherein the mask is a grid, a mesh or a stencil.

56. The method of paragraph 55 wherein the mask is a mesh.

57. The method of paragraph 56 wherein the mesh comprises one or more metals.

58. The method of any one of paragraphs 54 to 57 wherein the mask comprises one or more chromophore reflectors.

59. The method of paragraph 58 wherein the one or more chromophore reflectors is a glass bead, a gold flake, a metal particle, a mirrored glass bead, a salt crystal, a silica, or any combination thereof.

60. The method of any one of paragraphs 1 to 59 wherein the chromophore comprises carbon.

61. The method of any one of paragraphs 1 to 60 wherein the chromophore is a phase transition chromophore.

62. The method of paragraph 61 wherein the phase transition chromophore comprises paraffin.

63. The method of any one of paragraphs 1 to 62 wherein the specific pattern comprises one or more lines.

64. The method of any one of paragraphs 1 to 63 wherein the specific pattern is a wavy pattern.

Having thus described in detail preferred embodiments of the present invention, it is to be understood that the invention defined by the above paragraphs is not to be limited to particular details set forth in the above description, as many apparent variations thereof are possible without departing from the spirit or scope of the present invention.

What is claimed is:

1. A method for fractional wounding of skin, comprising:
applying at least one chromophore in a specific pattern to a predetermined area of the skin, wherein the specific pattern corresponds to a desired pattern of fractional wounding of the skin; and
applying electromagnetic radiation to the predetermined area of the skin so as to produce a plurality of thermally-damaged regions in an epidermal portion of the skin based on an interaction between the at least one chromophore and the electromagnetic radiation.

2. The method of claim 1, further comprising removing a first portion of the at least one chromophore from a surface of the skin prior to applying the electromagnetic radiation, wherein a second portion of the at least one chromophore remains in pores of the skin.

3. The method of claim 2 wherein the at least one chromophore is applied to the skin as a powder.

4. The method of claim 1 wherein the specific pattern is applied using at least one of a grid, a mesh, a roller, a stamp or a stencil.

5. The method of claim 1 wherein the specific pattern is applied using an attachment medium.

6. The method of claim 5 wherein the attachment medium is an adhesive.

7. The method of claim 5 wherein the attachment medium is light-activated.

8. The method of claim 6 wherein the attachment medium is at least one of an acrylide, a derma-bond or a glue.

9. A method for fractional wounding of skin, comprising;
applying at least one chromophore to a predetermined area of the skin; and
applying a mask with a specific pattern over the predetermined area of the skin, wherein the specific pattern corresponds to a desired pattern of fractional wounding of the skin; and
applying electromagnetic radiation to the predetermined area so as to generate regions of a thermal injury in an epidermal portion of the skin based on an interaction between the electromagnetic radiation and the at least one chromophore, wherein the regions are formed in a predetermined pattern.

10. The method of claim 9 wherein the mask is at least one of a grid, a mesh, a roller, a stamp or a stencil.

11. The method of claim 9 wherein the mask protects the skin from fractional wounding and wherein the fractional wounding occurs where the skin is not in contact with the mask.

12. The method of claim 11 wherein the mask is at least one of a grid, a mesh or a stencil.

13. The method of claim 11 wherein the mask comprises at least one chromophore reflector.

14. The method of claim 13 wherein the at least one chromophore reflector is at least one of a glass bead, a gold flake, a metal particle, a mirrored glass bead, a salt crystal, or a silica.

15. The method of claim 1 wherein the at least one chromophore comprises carbon.

16. The method of claim 1 wherein the at least one chromophore is a phase transition chromophore.

17. The method of claim 16 wherein the phase transition chromophore comprises paraffin.

18. The method of claim 1 wherein the specific pattern comprises at least one line.

19. The method of claim 1, wherein the electromagnetic radiation has properties to generate a thermal injury to at least one region of the tissue proximal to the at least one chromophore, while avoiding a generation of the thermal injury in at least a portion of the predetermined area.

20. The method of claim 1, wherein a smallest dimension of the plurality of thermally damaged regions of the tissue is between about 1 µm and about 1000 µm.

21. The method of claim 1, wherein a smallest dimension of the plurality of thermally damaged regions of the tissue is between about 100 µm and about 800 µm.

22. The method of claim 1, wherein a distance between adjacent ones of the thermally damaged regions of the tissue is between about 10 µm and about 2000 µm.

23. The method of claim 1, wherein the thermally-damaged regions are further produced in a dermal portion of the skin.

24. The method of claim 9, wherein the regions of the thermal injury are further generated in a dermal portion of the skin.

* * * * *